United States Patent
Olalde Rangel

(10) Patent No.: US 7,608,286 B2
(45) Date of Patent: Oct. 27, 2009

(54) PHYTO-NUTRACEUTICAL SYNERGISTIC COMPOSITION FOR HYPERLIPEDEMIC CONDITION

(75) Inventor: Jose Angel Olalde Rangel, 519 Cleveland St., Suite 101, Clearwater, FL (US) 33755

(73) Assignee: Jose Angel Olalde Rangel, Clearwater, FL (US)

( * ) Notice: Subject to any disclaimer, the term of this patent is extended or adjusted under 35 U.S.C. 154(b) by 2 days.

(21) Appl. No.: 11/461,172

(22) Filed: Sep. 21, 2006

(65) Prior Publication Data

US 2008/0279882 A1 Nov. 13, 2008

(51) Int. Cl.
*A01N 65/00* (2006.01)
*A61K 36/074* (2006.01)
*A61K 36/258* (2006.01)
*A61K 36/8962* (2006.01)
*A61K 36/79* (2006.01)
*A61K 36/638* (2006.01)
*A61K 36/254* (2006.01)
*A61K 36/233* (2006.01)
*A61K 36/746* (2006.01)
*A61K 31/722* (2006.01)
*A61K 36/068* (2006.01)
*A61K 36/815* (2006.01)

(52) U.S. Cl. .................. 424/725; 424/728; 424/729; 424/754

(58) Field of Classification Search .................. None
See application file for complete search history.

(56) References Cited

U.S. PATENT DOCUMENTS

| | | | | |
|---|---|---|---|---|
| 5,846,569 A | * | 12/1998 | Anderson et al. | 424/535 |
| 6,495,173 B1 | * | 12/2002 | Yegorova | 424/750 |
| 6,503,529 B1 | * | 1/2003 | Fleischner | 424/439 |
| 6,933,291 B2 | * | 8/2005 | Qi et al. | 514/171 |
| 7,135,199 B2 | * | 11/2006 | Kim et al. | 424/725 |
| 2003/0108591 A1 | * | 6/2003 | Meijer et al. | 424/439 |
| 2005/0163874 A1 | * | 7/2005 | Alexiev | 424/757 |
| 2005/0186296 A1 | * | 8/2005 | Palu et al. | 424/769 |
| 2005/0238654 A1 | * | 10/2005 | Takeda | 424/195.15 |
| 2006/0062863 A1 | * | 3/2006 | Ghosal | 424/757 |

FOREIGN PATENT DOCUMENTS

CN 1325703 A * 12/2001
WO WO 2004/082700 * 9/2004

OTHER PUBLICATIONS

Sun et al., The effect of Yishen Jiangzhi tablets on rats with hyperlipidemia, Chinese Journal of information on traditional Chinese medicine, 11 (1): 44-45, 2004.*

Cui et al., Treating fatty liver with Jiangzhitiaogan decoction, Chinese journal of information on traditional Chinese medicine, 12 (4): 71-72, 2005.*

* cited by examiner

*Primary Examiner*—Michele Flood
*Assistant Examiner*—Qiuwen Mi

(57) ABSTRACT

A Phytoceutical composition for the prevention and treatment of hyperlipidemia—cholesterol and triglyceride disorder—is provided. A specific combination of extracts of plants and nutraceuticals is taught, as well as principles for varying the formulations based on categorizing plants and nutraceuticals into one of three groups, Energy, Bio-Intelligence, and Organization and selecting several plants and nutraceuticals from each group. Such combinations have synergistic effects, with minimal side effects.

1 Claim, 1 Drawing Sheet

Figure 1: Plants and nutraceuticals classified under Energy, Intelligence and Organization principles; and according to classification listed in Table 1.
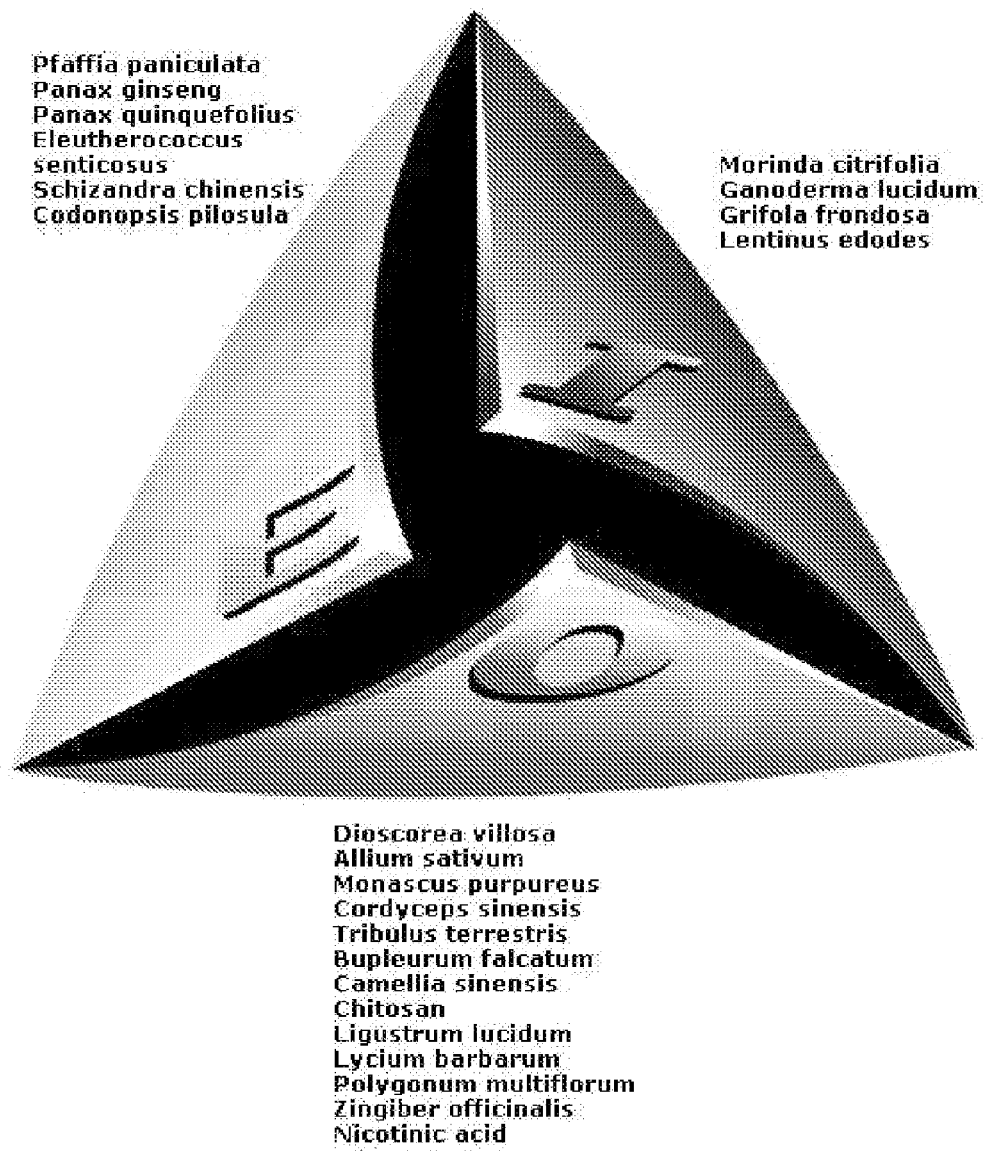

PHYTO-NUTRACEUTICAL SYNERGISTIC COMPOSITION FOR HYPERLIPEDEMIC CONDITION

PRIOR RELATED APPLICATIONS

Not applicable.

FEDERALLY SPONSORED RESEARCH STATEMENT

Not applicable.

REFERENCE TO MICROFICHE APPENDIX

Not applicable.

FIELD OF THE INVENTION

The invention relates to a phyto-nutraceutical formulation used to treat cholesterol and triglyceride disorders. The formulation is a particular combination of plants that have synergistic effect in combination. Principles for selecting beneficial formulation are provided.

BACKGROUND OF THE INVENTION

The academic study of medicinal plants for the treatment of diverse diseases has been nearly as pervasive as the study of Western medicines. The active principles from many traditional medicines have been extracted from plants, the curative agents identified and their mechanisms of action determined. Plant based medicines are typically well tolerated, with less severe side effects as well as a smaller range of side effects. In contrast, while synthetic drugs can be highly effective, their use is often hampered by severe side effects. Additionally, while synthetic pharmaceuticals are based upon single chemicals, many phytomedicines exert their beneficial effects through the additive or synergistic action of several chemical compounds acting at single or multiple target sites associated with a physiological process.

As pointed out by Tyler (1999), this synergistic or additive pharmacological effect can be beneficial by eliminating the problematic side effects associated with the predominance of a single xenobiotic compound in the body. In this respect, Kaufman et al. (1999) extensively documented how synergistic interactions underlie the effectiveness of a number of phytomedicines. This theme of multiple chemicals acting in an additive or synergistic manner likely has its origin in the functional role of secondary products in promoting plant survival. For example, in the role of secondary products as defense chemicals, a mixture of chemicals having additive or synergistic effects at multiple target sites would not only ensure effectiveness against a wide range of herbivores or pathogens but would also decrease the chances of these organisms developing resistance or adaptive responses (Kaufman et al., 1999; Wink, 1999). Conclusion: On one hand, synthetics may have the required efficacy for disease treatment; however this can be marred by severe side effects. On the other hand, despite the excellent medicinal qualities of many plants, they are individually insufficient to take chronic degenerative diseases into remission. However, there is mounting evidence which demonstrates that medical plants contain synergistic efficacy and/or side-effect neutralizing combinations (Gilani and Rahman, 2005). Thus, what are needed in the art are better treatment regimes with improved patient tolerance, while providing sufficient efficacy.

SUMMARY OF THE INVENTION

A number of known beneficial plants and tonics were classified according to their capacity to enhance the three main elements that support overall health: Energy (E), Bio-intelligence (I) and Organization (O). A synergistic effect is expected when all three categories of herbs (E, I, O) are included in a formulation, preferably at least two or three or four plants from each category. Thus, one embodiment of the invention provides the method of selecting the disease treating formulation according to these principles. An example of a formulation prepared this way is provided and additional formulations are being prepared and tested.

Another embodiment of the invention provides an effective, natural composition for treating high cholesterol and triglyceride levels.

The composition can be used alone, or can be combined with simultaneous use of one or more pharmaceutical compositions. It can be used for the treatment of atherosclerosis, hypercholesterolemia, hyperlipidemia, hypertrigliceridemia and other conditions associated with the excess of cholesterol and triglycerides in the blood.

DETAILED DESCRIPTION OF THE INVENTION

"Pharmaceutically acceptable excipients" is used herein according to art accepted meanings, and includes those ingredients needed to formulate a medicine for mammalian use, including the use of gelatin capsules.

"Synergistic" or "synergy" is used herein to mean that the effect is more than its additive property. In preferred embodiments, the synergy is at least 1.5, 2, 5, or 10 fold.

By use of "plants," what is meant herein is that the plant (or that portion with medicinal activity) is used whole, ground, or as an extract. Also included are purified active ingredients and derivatives thereof. However, it is believed that the best efficacy of plants used herein is achieved with the use of the entire plant or its extracts, rather than with the use of isolated active ingredients.

Further, although plants are named here according to commonly used nomenclature, with improving taxonomy plants are often reclassified. Whenever a plant is referenced, it includes related species with similar active ingredients.

The following examples are illustrative only and should not serve to unduly limit the invention.

EXAMPLE 1

Plant Characteristics

Cholesterol and Triglyceride Disorders

Energy Supplying Components.—

*Codonopsis pilosula* (Dang Shen, Fang Tang, Radix *Codonopsis*, bonnet bellflower, snerleklokke). Contains saponins, alkaloids, polysaccharides, glucose, stevioside, starch, scutellarein glucoside, Aspartic acid, and other 17 amino acids, amylose, minerals. Dang Shen is an important herb in Chinese medicine, where it's considered a tonic that increases energy levels and helps the body adapt to stress [Chevallier. A. *The Encyclopedia of Medicinal Plants* Dorling Kindersley. London 1996 ISBN 9-780751-303148]. The root is similar in action to ginseng (*Panax* species), but it's milder and has a shorter-lasting effect [Grieve. A Modern Herbal. Penguin 1984 ISBN 0-14-046-440-9; Kariyone. T. *Atlas of Medicinal Plants*; Yeung. Him-Che. *Handbook of*

*Chinese Herbs and Formulas.* Institute of Chinese Medicine, Los Angeles 1985; Duke. J. A. and Ayensu. E. S. *Medicinal Plants of China* Reference Publications, Inc. 1985 ISBN 0-917256-20-4; Bown. D. *Encyclopaedia of Herbs and their Uses.* Dorling Kindersley, London. 1995]. *C. pilosula* root extracts offer antioxidant activity, inhibiting erythrocyte hemolysis and lipid peroxidation (Ng T B, Liu F, Wang H X. The antioxidant effects of aqueous and organic extracts of *Panax quinquefolium, Panax notoginseng, Codonopsis pilosula, Pseudostellaria heterophylla* and *Glehnia littoralis.* J Ethnopharmacol. 2004; 93:285-8).

*Eleutherococcus* or *Acanthopanax senticosus* (Russian Ginseng, Siberian Ginseng, Eleuthero, Devil's Shrub, Buisson du Diable, Touch-me-not, Wild Pepper, Shigoka, *Acantopanacis senticosus*). Contains terpenoids (oleanolic acid), Eleutheroside A (daucosterol); Eleutheroside B (siringin); Eleutheroside B1 (isofraxidine); Eleutheroside B4 (sesamin); Eleutheroside D and E (heteroside siringoresinol); Eleutheroside C, G, I, K, L and M; phytosterols (β-sitosterol), polysaccharides (eleutherans), volatile oils, caffeic acid, coniferyl aldehyde, and sugars. Eleutherococcus, increases energy and vitality levels, improving physical and mental performance, and quality of life. It increases the contribution of oxygen to muscles and allows for longer exercising and faster recovery. Prevents fatigue. The adaptogenic effects of the root of eleutherococcus are produced by metabolic regulation of energy, nucleic acids, and tissular proteins. Eleuthero improves the formation of glucose-6-phosphate. The glucose-6-phosphate oxidizes by the way of pentose, producing substrates for the biosynthesis of nucleic acids and proteins. On the other hand, it increases the activity of succinate dehydrogenase and of muscular malate dehydrogenase, enzymes that intervene in the cycle of tricarboxilic acids, generating ATP. The Eleutherosides B and E are responsible for this adaptogenic activity. It has antioxidant activity as well. Russian Ginseng contains at least 40 active ingredients.

*Panax ginseng* (Chinese ginseng, *Panax*, ren shen, jintsam, ninjin, Asiatic ginseng, Japanese ginseng, Oriental ginseng, Korean red ginseng) The main active components are ginsenosides (protopanaxadiols and protopanaxatriols types) these have been shown to have a variety of beneficial effects, including anti-inflammatory and antioxidant effects. They also confer energizing properties because they increase ATP synthesis. A study reports that: oral administration of Korean red ginseng powder reduced plasma total cholesterol, triglyceride and NEFA, while increasing plasma HDL-cholesterol. The plasma lipid-improving actions were also observed in patients with hyperlipidemia. Hepatic cholesterol and triglyceride contents were decreased by ginseng administration, corresponding to improvement of the fatty liver (Yamamoto M, Uemura T, Nakama S. Serum HDL-cholesterol-increasing and fatty liver-improving actions of *Panax ginseng* in high cholesterol diet-fed rats with clinical effect on hyperlipidemia in man. Am J Chin Med. 1983; 11:96-101). *Panax* provides at least 86 active principles in a single therapeutic.

*Panax quinquefolius* (American Ginseng, Anchi, Canadian Ginseng, Five Fingers, Ginseng, American, North American Ginseng, Red Berry, Ren Shen, and Tienchi) is related to *Panax ginseng*, but is a distinct species with higher levels of ginsenoside Rb1 and without ginsenoside Rf. These substances confer energizing properties because they increase ATP synthesis. It has antioxidant and hypolipidemic effects. The incorporation of this phytomedicine provides at least 206 active principles in a single therapeutic.

*Pfaffia paniculata* (Suma, Brazilian Ginseng, *Pfaffia*, Para Tudo, Corango-acu; also *Hebanthe paniculata, Gomphrena paniculata, G. eriantha, Iresine erianthos, I. paniculata, I. tenuis, P. eriantha, Xeraea paniculata*) contains active glycosides (beta-ecdysone and three ecdysteroids), six different pfaffic acids, phytosterols (sitosterol and estigmasterol). *Pfaffia* also contains saponins and 19 different amino acids, minerals, vitamins and pantoneic acid. Its germanium content probably accounts for its properties as an oxygenator at the cellular level, and its high iron content may account for its traditional use for anemia. Its fitosterols offer hypolipemic effects. This herb increases energy through an increase in ATP synthesis and oxygenation at the cellular level, and it also has anabolic activity at the muscular level. Incorporation of *Pfaffia* provides at least 44 active principles in a single therapeutic.

*Schizandra chinensis* (*Schisandra spenenthera, Schisandra* berry, Chinese magnolia vine fruit, also known as Wuweizi and Wurenchum) The major active principles of *Schizandra* are lignans called Schizandrins. These substances have energizing properties because they increase the activity of some enzymes which participate in the oxidative phosphorylation process. *Schizandra* reduces fatigue and increase exercise resistance, it also has known hepato-protective and hepato-regenerative properties. *Schizandra* maintains the integrity of hepatocyte cellular membranes; increases hepatic levels of ascorbic acid; inhibits NADPH oxidation; inhibits lipid peroxidation at the hepatic microsomal level as well as formation of hepatic malondialdehyde; diminishes production of carbon monoxide at the hepatic level; has an inductor effect in the enzymatic anti-toxic microsomal hepatic cytochrome P-450; increases biliary flow and the excretion of toxic substances; promotes recovery of hepatic functions; induces mRNA formation for the Hepatocyte Growth Factor (HGF); encourages the proliferation of the hepatocyte's endoplasmic smooth reticula, and accelerates the proliferation of hepatocytes; increases ornithine decarboxylase activity as well as the mitotic index, facilitates DNA synthesis and hepatic proteins; increases levels of glutathione, glutathione reductase and glucose-6-phosphate, improving the regeneration capacity of the liver. The incorporation of this phytomedicine provides at least 81 active principles in a single therapeutic.

Bio-Intelligence Modulators.—

*Ganoderma lucidum* (Reishi, also *G. tsugae, G. valesiacum, G. oregonense, G. resinaceum, G. pfezfferi, G. oerstedli,* and *G. ahmadii*) is an edible fungus containing bitter triterpenoids (ganoderic acid), β-D-glucan, coumarins, alkaloids and ergosterols. The main hypolipemic principles of this mushroom are 26-oxygenosterols (ganoderol A, ganoderol B, ganoderal A, and ganoderic acid). These oxygenated sterols inhibit cholesterol biosynthesis, inhibiting "lanosterol 14alpha -demethylase", which converts 24 and 25-dihydrolanosterol to cholesterol (Hajjaj H, Mace C, Roberts M. Effect of 26-oxygenosterols from *Ganoderma lucidum* and their activity as cholesterol synthesis inhibitors. Appl Environ Microbiol. 2005; 71:3653-8). *Ganoderma* contains at least 32 active principles.

*Grifola frondosa* (Maitake, Dancing Mushroom; also *G. sordulenta, Polyporus umbellatus* and *Meripilus giganteus*) contains the primary polysaccharide, β-D-glucan in the 1.3 and 1.6 forms. It also contains alpha glucan, lipids, phospholipids, and ergosterol. A study demonstrated that *Grifola* lowered the serum total cholesterol level by enhancement of fecal cholesterol excretion. (Fukushima M, Ohashi T, Fujiwara Y. Cholesterol-lowering effects of maitake (*Grifola frondosa*) fiber, shiitake (*Lentinus edodes*) fiber, and enokitake (*Flammulina velutipes*) fiber in rats. Exp Biol Med (Maywood).

2001; 226:758-65). The incorporation of *Grifola* provides at least 6 active ingredients for therapeutic use.

*Lentinus edodes* (Hua gu, Shiitake, Shiitake mushroom) Its active principles are mostly present as glucans of different glycoside links, such as (1-->3), (1-->6)-beta-glucans y (1-->3)-alpha-glucans and as true heteroglicanes. Its active principles reduce VLDL, intermediate-density lipoprotein (IDL) y LDL-cholesterol concentration. Shiitake lowered the serum total cholesterol level by enhancement of fecal cholesterol excretion. (Fukushima M, Ohashi T, Fujiwara Y. Cholesterol-lowering effects of maitake (*Grifola frondosa*) fiber, shiitake (*Lentinus edodes*) fiber, and enokitake (*Flammulina velutipes*) fiber in rats. Exp Biol Med (Maywood). 2001; 226:758-65). Decreases of serum and liver Cholesterol concentrations.

Fecal excretion of several secondary bile acids and total bile acids increased (Sannoumaru Y, Shimizu J, Nakamura K. Effects of semi-purified dietary fibers isolated from *Lagenaria siceraria, Raphanus sativus* and *Lentinus edodes* on fecal steroid excretions in rats. J Nutr Sci Vitaminol (Tokyo). 1996; 42:97-110). Eritadenine, a compound found in the mushroom *Lentinus edodes*, significantly decreased the phosphatidylcholine (PC):phosphatidylethanolamine ratio in liver microsomes and the S-adenosylmethionine (SAM):S-adenosylhomocysteine (SAH) ratio in the liver, in addition to the plasma cholesterol concentration, supporting the hypothesis that the alteration of hepatic phospholipids metabolism may be a cause of the hypocholesterolaemic action of eritadenine. These observations suggest that the essential hypocholesterolaemic action of eritadenine might be associated with a modification of hepatic phospholipids metabolism rather than with the PC deficiency, due to the inhibition of PE N-methylation (Sugiyama K, Akachi T, Yamakawa A. Hypocholesterolaemic action of eritadenine is mediated by a modification of hepatic phospholipid metabolism in rats. J Nutr. 1995; 125:2134-44). The plasma free cholesterol level decreased in Shiitake-fed animals. Shiitake feeding resulted in a decrease in VLDL- and HDL-cholesterol. (Kabir Y, Yamaguchi M, Kimura S. Effect of shiitake (*Lentinus edodes*) and maitake (*Grifola frondosa*) mushrooms on blood pressure and plasma lipids of spontaneously hypertensive rats. J Nutr Sci Vitaminol (Tokyo). 1987; 33:341-6). It has been shown that *Ganoderma lucidum* and *Lentinus edodes* possess pronounced antiatherosclerotic properties (Li Khva Ren, Vasil'ev A V, Orekhov A N. Anti-atherosclerotic properties of higher mushrooms (a clinico-experimental investigation) Vopr Pitan. 1989; 1:16-9).

*Morinda citrifolia* (Noni, Indian Mulberry, Ba Ji Tian, Nono, Nonu, Fruta de Queso and Nhau) A large range of its components have been identified. Noni encompasses at least 23 active principles, 5 vitamins and 3 minerals. Among them: several acids, vitamins (A & C), potassium, Nordamnacanthal and Morindone, anthraquinones, fitosterols, flavonolglicosides, aucubine, alizarine and others. Noni protects against free radical damage as well as the ensuing lipid peroxidation. In one study, Noni's free radical scavenging properties was compared to three known antioxidants: vitamin C, grape seed powder and Picnogenol at the US RDA.

Noni capacity was 2.8 greater than vitamin C, 1.4 times greater than Picnogenol and 1.1 times that of the grape seed powder. Therefore, Noni offers a great potential to prevent lipid peroxidation. Another clinical double blind, randomized, placebo-controlled, one month long study, in smokers, reported that the levels of lipid hyperoxides and free radicals in a group administered Noni were 23% and 27% smaller respectively than the placebo group. The oxidative modification of low-density lipoprotein (LDL) plays an important role in the genesis of atherosclerosis. Another study determined that *Morinda*'s active principles inhibited the oxidation of LDL (Kamiya K, Tanaka Y, Endang H. Chemical constituents of *Morinda citrifolia* fruits inhibit copper-induced low-density lipoprotein oxidation. J Agric Food Chem. 2004; 52:5843-8). *Morinda* provides at least 31 active principles in a single therapeutic.

Organizational Improvers.—

*Allium sativum* (Garlic). Its main active principles are minerals (K, Ca, Fe, P, I), saccharose, vitamins (A, B1, B2, C, PP), essential oils and enzymes. The active principles which offer hypocholesterolaemic effects were: 2-vinyl-4h-1,3-dithiin, adenosine, ajoene, allicin, alliin, ascorbic-acid, beta-sitosterol, calcium, chromium, copper, diallyl-disulfide, diallyl-sulfide, diallyl-trisulphide, fiber, magnesium, nicotinic-acid, s-allyl-cysteine-sulfoxide, s-methyl-1-cysteine-sulfoxide. A study reported that the serum cholesterol and triglycerides were significantly reduced after eight weeks of treatment (Auer W, Eiber A, Hertkorn E, Hypertension and hyperlipidaemia: garlic helps in mild cases. Br J Clin Pract Suppl. 1990; 69:3-6). Another study reports: The postprandial increase of triglycerides was clearly reduced under garlic medication as compared to placebo treatment. Under garlic medication HDL2-cholesterol increased more than under placebo in tendency (Rotzsch W, Richter V, Rassoul F. Postprandial lipemia under treatment with *Allium sativum*. Controlled double-blind study of subjects with reduced HDL2-cholesterol. Arzneimittelforschung. 1992; 42:1223-7). *Allium* provides at least 184 active principles in a single therapeutic.

*Bupleurum falcatum* (*Bupleurum chinensis*, Saiko, Ch'ai hu, Beichaihu, bupleurum root, chaifu, chaiku-saiko, northern Chinese thorowax root, juk-siho, kara-saiko, mishima-saiko, nanchaihu, radix bupleur, saiko, shi ho, shoku-saiko, wa-saiko, Yamasaiko). Contains triterpene saponines (saiko-saponins A, B1 a B4, D, E, F, H); Saikogenines A-G and polysaccharides (Bupleurans 2IIb y 2IIc). Saponins from the plants of the genera *Bupleurum* inhibit the formation of lipid peroxides in the cardiac muscle or in the liver, they influence the function of enzymes contained in them, they decrease blood coagulation, cholesterol and sugar levels in blood (Purmova J, Opletal L. Phytotherapeutic aspects of diseases of the cardiovascular system. 5. Saponins and possibilities of their use in prevention and therapy. Ceska Slov Farm. 1995; 44:246-51). Saikosaponins isolated from the root of *Bupleurum falcatum* L. increased hepatic glycogen content, lowered plasma levels of cholesterol, triglycerides and phospholipids, increased fecal excretion of cholesterol (Yamamoto M, Kumagai A, Yamamura Y. Structure and action of saikosaponins isolated from *Bupleurum falcatum* L. II. Metabolic actions of saikosaponins, especially a plasma cholesterol-lowering action. Arzneimittelforschung. 1975; 25: 1240-3). The incorporation of this phytomedicine provides at least 26 active principles in a single therapeutic.

*Camellia sinensis* (Tea): Epidemiological and animal studies have found that green tea is associated with lower plasma cholesterol. More than 400 active principles in *Camelia* have been studied, however, those that explain its hypolipidemic properties are: ascorbic-acid, chlorogenic-acid, epicatechin, epigallocatechin gallate, rutin, lycopene, theanine, inositol, nicotinic-acid, pantothenic-acid, beta-ionone, calcium, copper, magnesium and fiber. A study showed that epigallocatechin gallate (EGCG) in *Camellia sinensis* increases LDL receptor binding activity (3-fold) and lowered the cellular cholesterol concentration (28%). EGCG significantly lowered cellular cholesterol synthesis, explaining the reduction in cellular cholesterol (Bursill C A, Roach P D. Modulation of cholesterol metabolism by the green tea polyphenol (-)-epigallocatechin gallate in cultured human liver (HepG2) cells. J Agric Food Chem. 2006; 54:1621-6). It has been demonstrated that the body weights of rats and their plasma triglyceride, cholesterol, and LDL-cholesterol have been significantly reduced by feedings of oolong, black, pu-erh, and green tea leaves. The experimental data indicated that the molecular mechanisms of fatty acid synthase gene suppression by tea polyphenols (EGCG, theaflavins) may invite down-regulation of EGFR/PI3K/Akt/Sp-1 signal transduction pathways (Lin J K, Lin-Shiau S Y. Mechanisms of hypolipidemic and anti-obesity effects of tea and tea polyphenols. Mol Nutr Food Res. 2006; 50:211-7). One study established corrective effect of tea catechins on the parameters of lipid metabolism (blood cholesterol, triglyceride and LDL levels), and antioxidant enzymes activity (Chanadiri T, Sanikidze T, Esaishvili M. Effectiveness of green tea catechins for the correction of the alimentary obesity in the experiment. Georgian Med. News. 2005:61-3). Green tea and its catechins consumptions: (i) decrease body weight by interfering within the sympathoadrenal system and fatty acid synthesis, (ii) decrease cholesterol absorption and plasma levels, (iii) have strong free radical-scavenging activity inhibiting LDL oxidation, (iv) reduce the adhesion molecule expression, (v) have antithrombotic activities by inhibiting platelet aggregation and (vi) decrease systolic and diastolic blood pressures (Hernandez Figueroa T T, Rodriguez-Rodriguez E, Sanchez-Muniz F J. The green tea, a good choice for cardiovascular disease prevention? Arch Latinoam Nutr. 2004; 54:380-94). Another study suggests that antioxidant epigallocatechin gallate (EGCG), the main antioxidant derived from green tea, differentially reduces evolving atherosclerotic lesions without influencing established atherosclerosis (Chyu K Y, Babbidge S M, Zhao X. Differential effects of green tea-derived catechin on developing versus established atherosclerosis in apolipoprotein E-null mice. Circulation. 2004; 109:2448-53). Green tea consumption was, statistically, significantly associated with lower levels of serum total cholesterol in both men and women (Tokunaga S, White I R, Frost C. Green tea consumption and serum lipids and lipoproteins in a population of healthy workers in Japan. Ann Epidemiol. 2002; 12:157-65). The incorporation of this phytomedicine provides at least 409 active principles in a single therapeutic.

Chitosan is derived by alkaline deacetylation from chitin, an abundant polymeric product of natural biosynthesis especially in crustaceans. Chitosan behaves as a polycationic (+) cellulose-like fibrillar biopolymer that forms films with negatively charged surfaces.

Chitosan binds lipids in the small intestine and reduces their absorption. Chitosan has been shown to decrease serum cholesterol in animal and human studies. Its principal active components are long molecules of amino polysaccharides (N-acetyl-D-glycosamine) that contain groups of free amino acids with positive electric charges, Negatively charged molecules in stomach attach strongly to the positive charged tertiary amino group ($-NH_3+$) of chitosan. Therefore, chitosan reduces fat absorption from gastrointestinal tract by binding with anionic carboxyl groups of fatty and bile acids, and it interferes with emulsification of neutral lipids (i.e., cholesterol, other sterols) by binding them with hydrophobic bonds. It is not specifically hydrolyzed by digestive enzymes in man. Furthermore, it competitively inhibits some pancreatic enzymes like lipases and amylases. Scientific evidence shows the capacity to eliminate lipids 5-10 times greater than other fibers, like cellulose, chitin or agar. Chitosan incorporated into bread formulations improved the lipoprotein balance, increased the HDL—and lowered the LDL—cholesterol (Ausar S F, Morcillo M, Leon A E, Ribotta P D. Improvement of HDL- and LDL-cholesterol levels in diabetic subjects by feeding bread containing chitosan. J Med. Food. 2003; 6:397-9). One Clinical, Randomized Controlled Trial showed that Chitosan significantly reduced total cholesterol compared to placebo. In a subgroup of subjects with over 60 years of age, chitosan group significantly reduced total and LDL cholesterol. (Bokura H, Kobayashi S. Chitosan decreases total cholesterol in women: a randomized, double-blind, placebo-controlled trial. Eur J Clin Nutr. 2003; 57:721-5). Dietary chitosan has been reported to reduce serum total cholesterol levels by 5.8-42.6% and low-density lipoprotein levels by 15.1-35.1%. (Ylitalo R, Lehtinen S, Wuolijoki E. Cholesterol-lowering properties and safety of chitosan. Arzneimittelforschung. 2002; 52: 1-7).

*Cordyceps sinensis* (Caterpillar fungus, Chongcao, *Cordyceps* spp., Deer fungus parasite). Contains polysaccharides that lower plasma triglyceride and cholesterol levels (Kiho T, Yamane A, Hui J. Polysaccharides in fungi. Biol Pharm Bull. 1996; 19:294-6); Nucleotides and Nucleosides, such as adenosine, uracil, uridine, guanine, guanosine, and 2'- and 3'-deoxyadenosine (cordycepin) (Shiao et al., 1994; Chen and Chu, 1996) that inhibit platelet aggregation (Ikumoto et al., 1991; Shiao et al., 1994) and have shown calcium antagonist activity (Furuya et al., 1983). *Cordyceps sinensis* also contains: galactomannans (Miyazaki et al., 1977; Kiho et al., 1986), polyamines (spermine, spermidine, homospermidine, putrescine, 1,3-diaminopropane) (Zhu and Masaru, 1993), various uncommon cyclic dipeptides, minerals, vitamins B1, B2, B12, E and K, all the essential amino acids (Yue et al., 1995; Huang et al., 1991; Xu et al., 1992; Guo, 1986; Tao, 1995; Xia et al., 1985), glutamic acid, Ltryptophan, L-arginine, and lysine (Zhang et al., 1991). Also, d-mannitol, ergosterol, ergosterol derivatives, alkaloids, fatty acids (mainly oleic, linoleic, palmitic, and stearic acids) (Shiao et al., 1989), and sterols (Kadota et al., 1986). Studies have demonstrated that *Cordyceps sinensis* helps lower total cholesterol by 10 to 21% and triglycerides by 9 to 26%. At the same time it helps to increase HDL-cholesterol by 27 to 30% and decrease the very low-density lipoprotein plus low-density lipoprotein (VLDL+LDL) cholesterol level. These studies show the main activities of the fungus in oxygen-free radical scavenging, antisenescence, hypolipidemic and antiatherosclerotic activities. (Zhu J S, Halpern G M, Jones K. The scientific rediscovery of an ancient Chinese herbal medicine: *Cordyceps sinensis*: part I. J Altern Complement Med. 1998; 4:289-303 and Koh J H, Kim J M, Chang U J. Hypocholesterolemic effect of hot-water extract from mycelia of *Cordyceps sinensis*. Biol Pharm Bull. 2003; 26:84-7). *Cordyceps* also prevents cholesterol deposition by inhibition of LDL oxidation mediated by free radicals (Yamaguchi Y, Kagota S, Nakamura K. Inhibitory effects of water extracts from fruiting bodies of cultured *Cordyceps sinensis* on raised serum lipid peroxide levels and aortic cholesterol deposition in atherosclerotic mice. Phytother Res. 2000; 14:650-2). The incorporation of this phytomedicine provides at least 35 active principles in a single therapeutic.

*Dioscorea villosa* (Mexican wild yam, china root, colic root, rheumatism root, huesos del diablo, yuma.) contains steroid sapogenins (dioscine, dioscorin and diosgenine) as the main active principles. It also contains salts and minerals, such as: aluminum, calcium, chrome, cobalt, iron, selenium, silica, sodium, tin, zinc, magnesium, manganese, phosphorus and potassium; and vitamins: ascorbic acid, beta-carotene, niacin, riboflavin and thiamine. The main active principles which explain its anti-oxidant properties are: diosgenine, ascorbic-acid and magnesium. Diosgenine reduces cholesterol levels through three mechanisms:

1) An anti-hypercholesterolemia mechanism which is probably related with its cholesterol absorption inhibitory activity. 2) Another major pathway for elimination of cholesterol is via secretion into bile. Biliary cholesterol secretion is stimulated by diosgenine. 3) Finally it inhibits HMG Co A reductase, an important enzyme in the cholesterol synthesis pathway, mechanism which is similar to synthetic pharmaceuticals such as statins. The incorporation of this phytomedicine provides at least 29 active principles in a single therapeutic.

*Ligustrum lucidum* (Glossy privet, Chinese Privet, Nepal Privet, Nu Chen, Nu Chen P'I Chiu, Nu-zhen-zi, To-Nezumi-Moti) Its main active principles are: Triterpenoids (Oleanolic Acid, Osolic Acid, Oleuropenin Denamite); Secoiridoid Glucosides (Lucidumoside, Oleoside dimethyl ether, Neonuezhenide, Oleuropein, Ligustrosides A and B, Isoneuzhenide, Lucidumosides A, B, C, and D). Also, ligustalosides, ligustrosidic acid, alpha-mannitol, oleanic and linolenic acids. These substances exhibit strong antioxidant effect against damage induced by free radicals. The active principles which explain its hypolipidemic properties are: linolenic-acid, oleic-acid, oleanolic-acid; and minerals calcium, copper and magnesium. (Peng Y. Prevention of experimental atherosclerosis in rabbits with *Ligustrum lucidum* fruit. Zhong Yao Tong Bao. 1983; 8:32-4. Incorporation of this phytomedicine in a composition provides at least 18 active principles in a single therapeutic.

*Lycium barbarum* (*Lycium chinense* MILL. (Solanaceae)—Chinese Boxthorn, Chinese Matrimony Vine, Chinese Wolfberry, Chinesischer Bocksdorn (Ger.), Daun Koki (Indones.), Gou Qi zi (Chin.), Kaukichai (Malays.), Kuko (Jap.), Lyciet de Chine (Fr.), Spina Santa Cinese (Ital.), Wolfberry) Goji, lycium fruit, bastard jasmine, tea tree). The main constituents of the fruits of *Lycium barbarum* L. are polysaccharides, flavonoids, phytosterols (Betasitosterol) and Cerebrosides. Polysaccharides reduce serum total cholesterol and triglyceride and increase High Density Lipoprotein cholesterol. (Luo Q, Cai Y, Yan J. Hypoglycemic and hypolipidemic effects and antioxidant activity of fruit extracts from *Lycium barbarum*. Life Sci. 2004; 76:137-49). Betasitosterol can prevent cholesterol absorption in the gastrointestinal tract (Law M. Plant sterol and stanol margarines and health. BMJ 2000; 320:861-4).

Total flavonoids of *Lycium barbarum* L. show free radicals scavenging effects (Huang Y, Tan A, Shen Y. Scavenging effect of total flavonoids of *lycium barbarum* L on active oxygen radicals and inhibitory effects on heat output from L1210 cells. Wei Sheng Yan Jiu. 1998; 27:109-11, 115). Incorporation of Lyceum provides at least 18 active principles in a single therapeutic.

*Monascus purpureus* (Red Yeast Rice) Red yeast rice forms naturally occurring hydroxymethylglutaryl-CoA reductase (HMG-CoA reductase) inhibitors known as monacolins. *Monascus* contains a family of nine different monacolins, all of which have the ability to inhibit HMG-CoA reductase. Other active ingredients include sterols (betasitosterol, campesterol, stigmasterol and sapogenin), isoflavones, and monounsaturated fatty acids. A Randomized Controlled Trial reports that Red Yeast Rice significantly reduced LDL-C, total cholesterol, triglycerides and apolipoprotein B levels, and was well tolerated in patients with hyperlipidemia. (Lin C C, Li T C, Lai M M. Efficacy and safety of *Monascus purpureus* Went rice in subjects with hyperlipidemia. Eur J Endocrinol. 2005; 153:679-86). 502 patients with hyperlipidemia were randomly assigned to two groups in a single-blinded clinical trial. 324 patients received a red yeast rice preparation and 122 patients received another Chinese herbal medicine, Jiagulan (*Gynostemma pentaphylla*) as a control. After eight weeks, patients in the treatment arm had statistically significant reductions in total cholesterol, triglycerides and LDL cholesterol as well as increases in HDL cholesterol when compared with the control arm (Wang J, et al. Multicenter clinical trial of the serum lipid-lowering effects of a *Monascus purpureus* (red yeast) rice preparation from traditional Chinese medicine. Current Therapeutic Research, Clinical & Experimental 1997; 58:964-978). 83 subjects with hyperlipidemia participated in a 12-week randomized controlled trial of red yeast rice supplementation. Subjects were randomized into two treatment arms to receive either 2.4 grams per day of red yeast rice or placebo. Total cholesterol and LDL cholesterol was significantly reduced in the treatment arm when compared to control after eight and 12 weeks. There were no reported side effects in the treatment arm (Heber D, et al. Cholesterol-lowering effects of a proprietary Chinese red-yeast-rice dietary supplement. Am J Clin Nutr 1999; 69:231-6). 14 subjects with dyslipidemia participated in a randomized controlled trial of *Monascus purpureus*. Subjects were randomized to receive either 1.2 grams *Monascus purpureus* twice daily or placebo for eight weeks. Among those who completed the protocol, significant declines from baseline in mean for fasting total cholesterol after two and eight weeks and for LDL cholesterol after eight weeks were observed. (Keithley J K, Swanson B, Sha B E, Zeller J M, Kessler H A, Smith K Y. A pilot study of the safety and efficacy of cholestin in treating HIV-related dyslipidemia. Nutrition 2002; 18:201-4). *Monascus* provides 18 active principles in a single therapeutic.

Niacin (Nicotinic acid, vitamin B3) Niacin is a part of the normal diet that is essential to various chemical reactions in the body. It is used medically to treat individuals with deficiency of niacin. Advanced deficiency of niacin can lead to a condition called pellagra in which individuals develop diarrhea, dermatitis and dementia. Niacin also is used to reduce cholesterol and triglyceride levels in the blood. Specifically it reduces LDL cholesterol and increases HDL-cholesterol. It is not clear how niacin causes its effects on cholesterol and triglyceride levels, but it may be by reducing the production of proteins that transport cholesterol and triglycerides in the blood. High doses of nicotinic acid effectively raise HDL-C levels. A low dose (1.5 g/d) of nicotinic acid causes an average 20% increase in HDL-C levels and significantly lowers triglyceride levels in both normolipidemic and hyperlipidemic patients with low HDL-C levels (Martin-Jadraque R, Tato F, Mostaza J M. Effectiveness of low-dose crystalline nicotinic acid in men with low high-density lipoprotein cholesterol levels. Arch Intern Med. 1996; 156:1081-8). 63 participants having low blood concentrations of high-density lipoprotein cholesterol (HDL-C) were treated with low-dose, time-release nicotinic acid in a controlled study, HDL-C levels increased a mean of 18% (+6 mg/dl), total cholesterol concentrations decreased 9% (−20 mg/dl), the ratio of total cholesterol to HDL-C decreased 25%, low-density lipoprotein cholesterol levels decreased 13%, and triglyceride levels decreased 20%. (Squires R W, Allison T G, Gau G T. Low-dose, time-release nicotinic acid: effects in selected patients with low concentrations of high-density lipoprotein cholesterol. Mayo Clin Proc. 1992; 67:855-60).

*Polygonum multiflorum* (Fo-Ti, Chinese Knotweed, Chinese Cornbind, Climbing Knotweed, Flowery Knotweed, Fleeceflower, He Shou Wu) The main constituents of *Polygonum multiflorum* are: emodin, chrysophanol, rhein, 6-OH-emodin, emodin-8-beta-D-glucoside, polygonimitin B, 2,3,5,4'-tetrahydroxystilbene-2-O-beta-D-glucoside, gallic acid. *Polygonum multiflorum* stilbeneglycoside reduces plasma cholesterol, low-density lipoprotein cholesterol, very low-density lipoprotein cholesterol, and plasma triglyceride. It also decreases atherosclerotic injured areas (Yang P Y, Almofti M R, Lu L. Reduction of atherosclerosis in cholesterol-fed rabbits and decrease of expressions of intracellular adhesion molecule-1 and vascular endothelial growth factor in foam cells by a water-soluble fraction of *Polygonum multiflorum*. J Pharmacol Sci. 2005; 99:294-300). Two studies show the antioxidant activity of *Polygonum*: inhibited oxygen consumption, malonaldehyde production and radical scavenging effects. -2,3,5,4'-tetrahydroxystilbene-2-O-beta-d-glucopyranoside is the active constituent responsible for the antioxidant property (Hong C Y, Lo Y C, Tan F C. *Astragalus membranaceus* and *Polygonum multiflorum* protect rat heart mitochondria against lipid peroxidation. Am J Chin Med. 1994; 22:63-70); (Ryu G, Ju J H, Park Y J. The radical scavenging effects of stilbene glucosides from *Polygonum multiflorum*. Arch Pharm Res. 2002; 25:636-9). *Polygonum* provides at least 47 active principles in a single therapeutic.

*Tribulus terrestris* (Caltrop, Yellow Vine, bindy eye, bindii, bullhead, burnut, burra gokhroo, caltrop, calthrops, cat's head, common dubbeltjie, devil's thorn, devil's weed, doublegee, dubbeltje, goathead, gokshura, ground bur-nut, isiHoho, land caltrop, Maltese cross, Mexican sandbur, puncture vine, puncture weed, rose, small caltrops, tackweed, Texas sandbur, yellow vine and Goathead). The fruits and roots of *Tribulus* contain active principles such as: phytosterols, flavonoids, alkaloids, glucosides and steroidal saponins of the furostanol sub-class. These active principles could significantly lower the levels of serum Total cholesterol, LDL-c and liver Total cholesterol, triglycerides, and increase the activities of superoxide-dismutase (SOD) in liver (Chu S, Qu W, Pang X. Effect of saponin from *Tribulus terrestris* on hyperlipidemia. Zhong Yao Cai. 2003; 26:341-4); (Li M, Qu W, Chu S. Effect of the decoction of *tribulus terrestris* on mice gluconeogenesis. Zhong Yao Cai. 2001; 24:586-8). *Tribulus* provides at least 47 active principles in a single therapeutic.

*Zingiber officinalis* (Ginger) Contains 4-7.5% oleoresin with essential oil and sharp substances. The essential oil (1.5-3% of the drug) has a variable composition, according to its origin. The principal components are sesquiterpens such as a-zingiberen, arcurcumene, bisabolen, bisabolone, (EE)-a-pharnesene and sesquiphelandren, and monotherpenes like camphor, phelendren, geranial, neral and linalol. The sharp substances are gingerols and sogaols. They are non volatile phenilalcanones or phenilalcanonoles with chains of a different length, being the most important ones the (6)-gingerol and the (6) sogaol. The rhizome of ginger contains also diaryl-heptanoids: diphenylheptenones, diphenylheptanonoles, diphenylheptanodioles and their acetates. Other components are: starch (approximately 50%), ditherpenes, 6-gingesulphonic acid and monoacyl digalactosyl glycerols. *Zingiber* produced a significant reduction in serum total cholesterol, triglycerides, serum lipoproteins, phospholipids and increased HDL-cholesterol (Kadnur S V, Goyal R K. Beneficial effects of *Zingiber officinale* Roscoe on fructose induced hyperlipidemia and hyperinsulinemia in rats. Indian J Exp Biol. 2005; 43:1161-4); (Bhandari U, Sharma J N, Zafar R. The protective action of ethanolic ginger (*Zingiber officinale*) extract in cholesterol fed rabbits. J Ethnopharmacol. 1998; 61:167-71); (Bhandari U, Kanojia R, Pillai K K. Effect of ethanolic extract of *Zingiber officinale* on dyslipidaemia in diabetic rats. J Ethnopharmacol. 2005; 97:227-30). The active compounds of *Z. officinale* Roscoe inhibit the intestinal absorption of dietary fat by inhibiting its hydrolysis (Han L K, Gong X J, Kawano S. Antiobesity actions of *Zingiber officinale* Roscoe. Yakugaku Zasshi. 2005; 125:213-7). *Zingiber officinale* Roscoe active principles show an antioxidant activity due to not only radical scavenging activity of antioxidants but by affinity of the antioxidants to the substrates (Masuda Y, Kikuzaki H, Hisamoto M. Antioxidant properties of gingerol related compounds from ginger. Biofactors. 2004; 21:293-6). *Zingiber* provides at least 270 active principles in a single therapeutic.

EXAMPLE 2

Composition

Cholesterol and Triglyceride Disorders

A particularly preferred composition is shown in Table 1. Ratios reflect the concentration of active ingredient over the natural state, and the amounts provided are mg of extract. Obviously, the amount should be increased where the strength is reduced, and vice versa.

A particularly preferred composition is shown in Table 1.

TABLE 1

| Composition | | |
|---|---|---|
| Active Agent | Ratio | Amount (mg) |
| Energy enhancers | | |
| Codonopsis pilosula | 5:1 | 17.18 |
| Eleutherococcus senticosus | 5.1 | 14 |
| Panax ginseng | 5:1 | 14 |
| Panax quinquefolius | 4:1 | 54 |
| Pfaffia paniculata | 4:1 | 86 |
| Schizandra chinensis | 1:1 | 42.96 |
| Bio-Intelligence modulators | | |
| Ganoderma lucidum | 5:1 | 103 |
| Grifola frondosa | 5:1 | 103 |
| Lentinus edodes | 5:1 | 103 |
| Morinda citrifolia | 5:1 | 69 |
| Organization improvers | | |
| Allium sativum | 1:1 | 14 |
| Bupleurum chinense | 5:1 | 17.18 |
| Camelia sinensis | 5:1 | 17.18 |
| Chitosan | 5:1 | 17.18 |
| Cordyceps sinensis | 5:1 | 103 |
| Dioscorea villosa | 5:1 | 17 |
| Ligustrum lucidum | 5:1 | 8.59 |
| Lycium barbarum | 5:1 | 8.59 |
| Monascus purpureus | 1:1 | 42.96 |
| Niacin | 1:1 | 8 |
| Polygonum multiflorum | 5:1 | 8.59 |
| Tribulus terrestris | 5:1 | 23 |
| Zingiber officinalis | 5:1 | 8.59 |
| Total | | 900 |

EXAMPLE 3

Cholesterol and Triglyceride Disorders Effectiveness and Tolerance

Study One

The response of this composition was examined through a 3 month long retrospective, descriptive, multicenter study with 125 patients with high cholesterol and triglycerides. The administration of the composition significantly reduced the level of cholesterol and triglycerides in 80 and 88.8% of the patients respectively. Only 3.2% of the study group observed mild secondary effects, which did not warrant suspension of treatment. The formula was considered an interesting alternative which with a combination of diet, exercise and other treatments may produce an unexpectedly superior therapeutic answer to this disorder.

EXAMPLE 4

Principles for Selecting Synergistic Combinations

In order to explain the range of formulations encompassed by the invention, we have categorized beneficial plants and nutraceuticals into one of three groups, each of which should be present for synergistic effect. The classifications are: Energy, Bio-Intelligence and Organization. Plants and nutraceuticals classified under Energy are associated with ATP synthesis (such as the Krebs cycle, oxidative phosphorylation, beta-oxidation, etc.). Plants and nutraceuticals classified under Bio-Intelligence are those that regulate the neuroendocrine and immunological systems and cellular processes, thus controlling the interactions between the various systems in the body. Finally, plants and nutraceuticals classified under Organization are those that relate to the structure and function of specific organs. Combinations of plants and nutraceuticals from these three classification groups have synergistic effect because they address each necessary component of cellular and organic health—in effect they provide the triangle on which healing is fully supported. FIG. 1, depicts these components—plants and/or nutraceuticals—which enhance Energy (E), modulate Bio-Intelligence (I) and improve Organization (O); sides of the aforementioned health triangle. That is, the components listed on the left hand view of FIG. 1, are the plants and/or nutraceuticals which enhance Energy. The plants and/or nutraceuticals in the right view are those which improve Organization. Finally, the plants and nutraceuticals at the bottom view of FIG. 1 modulate Bio-Intelligence.

An illustrative example of synergy in medicinal plants is an in vitro study that demonstrates how the activity of herbal Berberine alkaloids is strongly potentiated by the action of 5'-methoxyhydnocarpin (5'-MHC)—an active principle of another phytomedicine (denominated Hydnocarpus wightiana). It shows a strong increase of accumulation of berberine in the cells in the presence of 5'-MHC, indicating that this plant compound effectively disabled the bacterial resistance mechanism against the berberine antimicrobial, thus showing the synergy of both substances. Stermitz F R, et al., Synergy in a medicinal plant: antimicrobial action of berberine potentiated by 5'-methoxyhydnocarpin, a multidrug pump inhibitor. Proc Natl Acad Sci USA. 2000; 97: 1433-7.

A further demonstration may be provided of synergistic effect on a molecular scale by studying the gene expression profile changes in response to various plant ingredients and combinations thereof. Experiments are already underway demonstrating the expression profile in response to the formulations. We will be aided in this work because researchers have already begun studying the expression profiles of various medicinal plants, thus providing a database of knowledge from which to build. E.g., Gohil, et al., mRNA Expression Profile of a Human Cancer Cell Line in Response to *Ginkgo Biloba* Extract: Induction of Antioxidant Response and the Golgi System, Free Radic Res. 2001; 33:831-849.

Finally there may be further presentation of gene expression results using whole-genome microarray analysis to demonstrate the formulation's capability to provide gene activation (upregulation or downregulation).

What is claimed is:

1. A phytoceutical composition for treating hyperlipidemia comprising: *Codonopsis pilosula*, 17.18 mg; *Eleutherococcus senticosus*, 14 mg; *Panax ginseng*, 14 mg; *Panax quinquefolius*, 54 mg; *Pfaffia paniculata*, 86 mg; *Schizandra chinensis*, 42.96 mg; *Ganoderma lucidum*, 103 mg; *Grifola frondosa*, 103 mg; *Lentinus edodes*, 103 mg; *Morinda citrifolia*, 69 mg; *Allium sativum*, 14 mg; *Bupleurum chinense*, 17.18 mg; *Camellia sinensis*, 17.18 mg; *Chitosan*, 17.18 mg; *Cordyceps sinensis*, 103 mg; *Dioscorea villosa*, 17 mg; *Ligustrum lucidum*, 8.59 mg; *Lycium barbarum*, 8.59 mg; *Monascus purpureus*, 42.96 mg; *Niacin*, 8 mg; *Polygonum multiflorum*, 8.59 mg; *Tribulus terrestris*, 23 mg; and *Zingiber officinalis* 8.59 mg; together with pharmaceutically acceptable excipients.

* * * * *